1 United States Patent
Okaguchi (10) Patent No.: US 11,773,835 B2
(45) Date of Patent: Oct. 3, 2023

(54) FLUID CONTROL DEVICE AND SPHYGMOMANOMETER

(71) Applicant: Murata Manufacturing Co., Ltd., Kyoto (JP)

(72) Inventor: Kenjiro Okaguchi, Kyoto (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 1063 days.

(21) Appl. No.: 16/508,856

(22) Filed: Jul. 11, 2019

(65) Prior Publication Data

US 2019/0331101 A1 Oct. 31, 2019

Related U.S. Application Data

(63) Continuation of application No. PCT/JP2018/001291, filed on Jan. 18, 2018.

(30) Foreign Application Priority Data

Jan. 20, 2017 (JP) .................................. 2017-008772

(51) Int. Cl.
*F04B 17/00* (2006.01)
*A61B 5/021* (2006.01)
*A61B 5/0225* (2006.01)

(52) U.S. Cl.
CPC .......... *F04B 17/003* (2013.01); *A61B 5/0225* (2013.01); *A61B 5/02141* (2013.01)

(58) Field of Classification Search
CPC ...... F04B 17/003; F04B 17/03; F04B 43/095; F04B 49/06; F04B 49/08; A61B 5/02141;
(Continued)

(56) References Cited

U.S. PATENT DOCUMENTS

2005/0219288 A1 10/2005 Vogeley et al.
2007/0242427 A1 10/2007 Yamamoto et al.
(Continued)

FOREIGN PATENT DOCUMENTS

JP 2007-533902 A 11/2007
JP 2010-148325 A 7/2010
(Continued)

OTHER PUBLICATIONS

International Search Report for International Application No. PCT/JP2018/001291, dated Mar. 20, 2018.
(Continued)

*Primary Examiner* — Matthew Kremer
*Assistant Examiner* — Kyle W. Kretzer
(74) *Attorney, Agent, or Firm* — Pearne & Gordon LLP (57) ABSTRACT

Provided are a fluid control device capable of operating a piezoelectric pump even in a case where a low discharge pressure or a slow pressurization speed is required and a sphygmomanometer including the fluid control device. A fluid control device includes a piezoelectric pump that includes a piezoelectric element, a self-excited circuit that performs, upon application of a driving power source voltage thereto, self-excited oscillation to drive the piezoelectric element, a switch that interrupts the driving power source voltage for the self-excited circuit, and a control circuit that changes an on duty ratio of the self-excited circuit by switching between states of the switch at a predetermined switching frequency and a predetermined on duty ratio.

15 Claims, 7 Drawing Sheets

(58) Field of Classification Search
CPC .......... A61B 5/0225; A61B 2560/0214; A61B 5/022; A61B 5/02255; A61B 5/02225
See application file for complete search history.

(56) References Cited

U.S. PATENT DOCUMENTS

| | | | |
|---|---|---|---|
| 2014/0285065 A1* | 9/2014 | Okaguchi | H10N 30/802 310/317 |
| 2014/0309541 A1* | 10/2014 | Yamashita | A61B 5/02233 600/485 |
| 2015/0038858 A1* | 2/2015 | Ariga | A61B 5/02255 600/490 |
| 2018/0108825 A1* | 4/2018 | Chen | F04B 49/06 |
| 2018/0132732 A1* | 5/2018 | Lin | F04B 19/006 |

FOREIGN PATENT DOCUMENTS

| | | |
|---|---|---|
| JP | 2013-220288 A | 10/2013 |
| JP | 2014-034951 A | 2/2014 |
| JP | 2014-144201 A | 8/2014 |
| WO | 2005/080793 A1 | 9/2005 |
| WO | 2013/157394 A1 | 10/2013 |

OTHER PUBLICATIONS

Written Opinion for International Application No. PCT/JP2018/001291, dated Mar. 20, 2018.

* cited by examiner

FLUID CONTROL DEVICE AND SPHYGMOMANOMETER

This is a continuation of International Application No. PCT/JP2018/001291 filed on Jan. 18, 2018 which claims priority from Japanese Patent Application No. 2017-008772 filed on Jan. 20, 2017. The contents of these applications are incorporated herein by reference in their entireties.

BACKGROUND

Technical Field

The present disclosure relates to a fluid control device including a piezoelectric pump and a sphygmomanometer including this fluid control device.

An existing fluid control device that controls a fluid by driving a piezoelectric element included in a piezoelectric pump is described in, for example, Patent Document 1. The device described in Patent Document 1 includes a boost regulator that boosts a battery voltage and an H bridge circuit that drives a piezoelectric element for both positive and negative polarities by using as a power source a voltage boosted by the boost regulator.

Patent Document 1: International Publication No. 2013/157394

BRIEF SUMMARY

According to the fluid control device that drives the piezoelectric element by using the H bridge circuit as described in Patent Document 1, the battery voltage is boosted by the boost regulator, and the piezoelectric element is driven by the H bridge circuit at a peak to peak voltage that is two times the output voltage of the boost regulator. Thus, even when the battery voltage is low, the piezoelectric element is driven at a predetermined high voltage.

In contrast, in order to operate the piezoelectric pump such that the discharge pressure becomes low, it is necessary to lower the driving voltage of the piezoelectric element. However, for this reason, when the power source voltage of the H bridge circuit is set too low, the H bridge circuit does not operate. This is because the H bridge circuit has transistors at both of an upper arm and a lower arm, has a configuration in which the transistors are connected in a shunt direction in a cascade manner, and has a constraint on its lowest driving voltage. In addition, in a case where a driving circuit for a piezoelectric element includes a circuit using, for example, an operational amplifier that operates at low voltage, it is difficult to increase the dynamic range of the operational amplifier in semiconductor processing such that the piezoelectric element operates even at low voltage. In this manner, in any case, there is a limit on the extent to which the driving voltage of the piezoelectric element is reduced.

For example, in the case of a sphygmomanometer for newborns, if the pressurization speed of the cuff is not sufficiently slowed down, the cuff pressure immediately increases after the pressurization is started and blood pressure measurement is not accurately performed.

The present disclosure provides a fluid control device capable of operating a piezoelectric pump even in a case where a low discharge pressure or a slow pressurization speed are required, and a sphygmomanometer including the fluid control device.

(1) A fluid control device according to the present disclosure includes a piezoelectric pump that includes a piezoelectric element, a self-excited circuit that performs, upon application of a driving power source voltage thereto, self-excited oscillation to drive the piezoelectric element, and a control circuit that determines an on duty ratio for driving the piezoelectric element.

With the configuration described above, the piezoelectric element is driven while a constraint on the lowest driving power source voltage for the self-excited circuit is satisfied, and thus self-excited oscillation does not stop and the self-excited circuit operates through duty control. Thus, the pressurization speed of the piezoelectric pump can be slowed down by using the on duty ratio. As a result, an operation is stably performed even at low pressure at which it has been impossible so far to stably perform the operation. In addition, an active element of the self-excited circuit operates in a saturation region, and thus operation is highly efficiently performed and heat generation of the active element is reduced.

(2) The fluid control device can include a switch that interrupts a driving voltage for the piezoelectric element, and the control circuit switches between states of the switch at a predetermined on duty ratio. With this configuration, the driving voltage for the piezoelectric element is switched between on and off at high speed, and thus fluid control is performed by the piezoelectric pump with high accuracy.

(3) The switch can include a FET or a FET and a circuit that drives the FET. As a result, it becomes easy to reduce cost and do miniaturization.

(4) The fluid control device can further include a DC/DC converter that controls the driving power source voltage, and the control circuit controls, in a range in which a necessary pressure is below a predetermined value, the on duty ratio in a state in which the driving power source voltage is set to the lowest voltage at which the self-excited circuit is operable, and controls, in a range in which the necessary pressure is greater than or equal to the predetermined value, the driving power source voltage in a voltage range higher than the lowest voltage in a state in which the on duty ratio is 100%. As a result, the self-excited circuit operates continuously in a region where the discharge pressure of the piezoelectric pump is high, thereby increasing the pressurization speed. In addition, in a case where the DC/DC converter performs a boost operation, for example, even when the voltage of a direct current input power source such as a battery is in a lower region, the self-excited circuit can be operated properly. In addition, the driving voltage of the self-excited circuit increases in a region where the discharge pressure of the piezoelectric pump is high, thereby increasing the pressurization speed.

(5) The control circuit can include a MCU including a PWM signal generation circuit that generates a PWM signal, and the on duty ratio is determined using the PWM signal. With this configuration, the circuit for controlling the on duty ratio and control thereof are simplified.

(6) A sphygmomanometer according to the present disclosure includes a cuff, a fluid control device that pressurizes the cuff, a valve that adjusts pressure inside the cuff, and a measurement unit that measures a blood pressure on the basis of a pulse wave or Korotkoff sounds and the pressure of the cuff, and the fluid control device includes a piezoelectric pump that includes a piezoelectric element, a self-excited circuit that performs, upon application of a driving power source voltage thereto, self-excited oscillation to drive the piezoelectric element, a switch that interrupts the driving power source voltage for the self-excited circuit, and a control circuit that changes an on duty ratio of the self-excited circuit by switching between states of the switch at a predetermined switching frequency and a predetermined on duty ratio.

With the configuration described above, an operation is stably performed even at low pressure at which it has been impossible so far to stably perform the operation. In addition, a highly efficient operation is performed and a low heat-generating operation is performed.

(7) The switching frequency can be a frequency within a range that is greater than or equal to ten times the reciprocal of a measurement period of the measurement unit and that is less than or equal to one tenth a driving frequency of the piezoelectric element. In this manner, when the switching frequency is greater than or equal to ten times the reciprocal of the measurement period, a decrease in the accuracy of measurement through duty ratio control can be practically eliminated. In addition, when the switching frequency is a frequency within a range that is less than or equal to one tenth the driving frequency of the piezoelectric element, a harmonic component caused by interruptions performed by the self-excited circuit does not practically affect the driving frequency of the piezoelectric element, and thus a decrease in the driving efficiency of the piezoelectric element is reduced.

According to the present disclosure, a fluid control device capable of operating a piezoelectric pump at a low discharge pressure or a slow pressurization speed and a sphygmomanometer including the fluid control device are constituted.

DETAILED DESCRIPTION

Hereinafter, a plurality of embodiments for exploitation of the present disclosure will be described by taking for example some specific examples with reference to the drawings. The same portions in the drawings will be denoted by the same reference numerals. By considering the ease of describing or understanding main points, a division into a plurality of embodiments are made and illustrated for the sake of convenience; however, it is possible to partially exchange between or combine configurations described in different embodiments. In the description of each of the embodiments, a redundant description about things in common will be omitted and in particular different points will be described. In addition, substantially the same operations and effects based on substantially the same configuration will not be stated one by one in every embodiment.

First Embodiment

Figure 1:
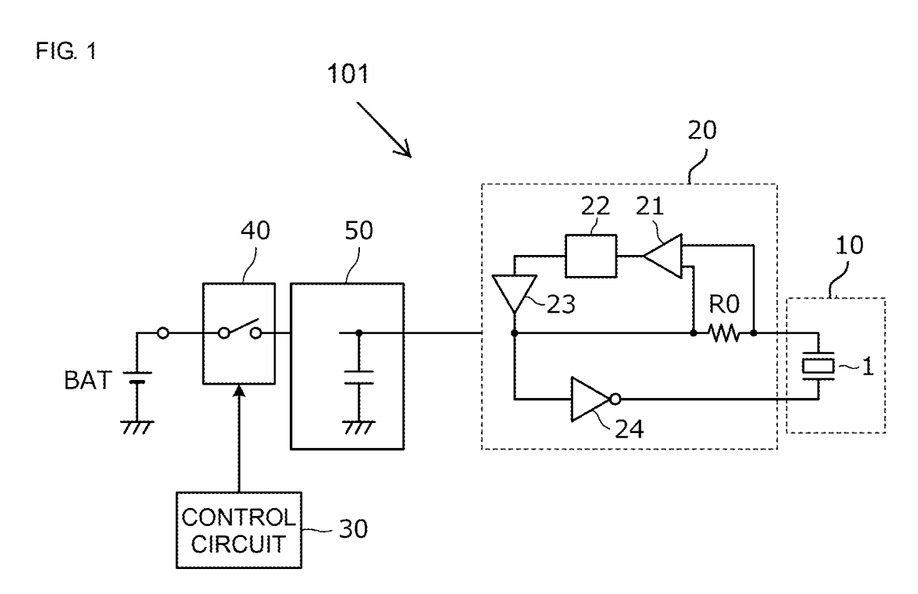
FIG. 1 is a block diagram illustrating the configuration of a fluid control device 101 according to a first embodiment.

FIG. 1 is a block diagram illustrating the configuration of a fluid control device 101 according to a first embodiment. The fluid control device 101 includes a piezoelectric pump 10, a self-excited circuit 20, a switch 40, and a control circuit 30. The piezoelectric pump 10 includes a piezoelectric element 1. The self-excited circuit 20 performs, upon application of a driving power source voltage thereto, self-excited oscillation to drive the piezoelectric element 1. The switch 40 interrupts the driving power source voltage for the self-excited circuit 20 (switches between application and non-application of the driving power source voltage). The control circuit 30 switches between states of the switch 40. In addition, the fluid control device 101 further includes a DC/DC converter 50 in the present embodiment.

An input power source BAT illustrated in FIG. 1 is a battery, and the DC/DC converter 50 boosts this input power source voltage to apply the driving power source voltage to the self-excited circuit 20. The self-excited circuit 20 performs self-excited oscillation with this driving power source voltage and applies an alternating voltage to the piezoelectric element 1.

The control circuit 30 switches between the states of the switch 40 at a predetermined switching frequency and a predetermined on duty ratio, and gradually increases the on duty ratio in accordance with time elapsed from the startup of the fluid control device 101.

Figure 2:
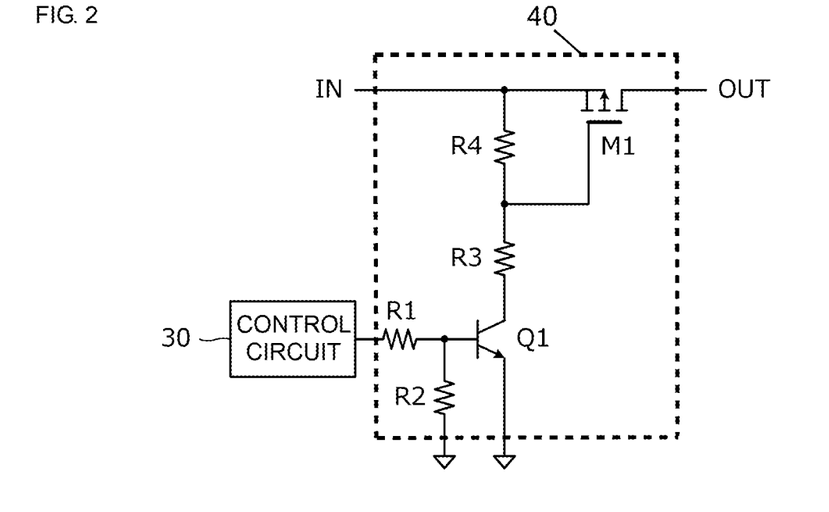
FIG. 2 is a circuit diagram of a switch 40.

FIG. 2 is a circuit diagram of the switch 40. The switch 40 includes a P-channel MOS-FET M1, resistors R4 and R3, a bipolar transistor Q1, and resistors R1 and R2. The transistor R4 generates the gate-source voltage of the P-channel MOS-FET M1. The base voltage of the transistor Q1 is applied to the resistor R1.

In FIG. 2, when the control circuit 30 outputs a "H" voltage, the transistor Q1 is turned on and the FET M1 is turned on (conducted). In contrast, when the control circuit 30 outputs a "L" voltage, the transistor Q1 is turned off and the FET M1 is turned off (blocked).

In FIG. 1, the self-excited circuit 20 includes an output current detection resistor R0, a differential amplifier circuit 21, a filter 22, a comparator 23, and a phase inversion comparator 24. The differential amplifier circuit 21 differentially amplifies a voltage drop across the resistor R0. The filter 22 allows a self-excited oscillation frequency to pass therethrough and attenuates the other unnecessary frequency component. The comparator 23, which is a one-input comparator, converts an output voltage of the filter 22 into a binary voltage signal. The phase inversion comparator 24 inverts the phase (the polarity) of an output voltage of the comparator 23. The output voltage of the comparator 23 is input to a first end of the piezoelectric element 1 via the resistor R0, and the output voltage of the phase inversion comparator 24 is input to a second end of the piezoelectric element 1.

With the circuit configuration described above, the current flowing in the piezoelectric element 1 and the voltage applied across the piezoelectric element 1 are in a positive feedback relationship, thereby performing self-excited oscillation. As a result, an alternating voltage having both positive and negative polarities is applied to the piezoelectric element 1.

Figure 3:
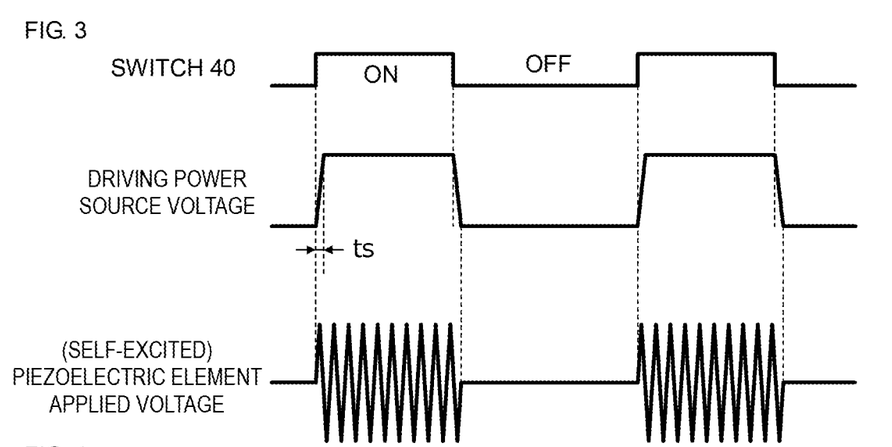
FIG. 3 is a waveform diagram illustrating a duty operation of a self-excited circuit 20.

FIG. 3 is a waveform diagram illustrating a duty operation of the self-excited circuit 20. When the switch 40 is on, the driving power source voltage is applied to the self-excited circuit 20. When the switch 40 is off, the driving power source voltage for the self-excited circuit 20 is blocked. That is, when the switch 40 is turned on, the driving power source voltage for the self-excited circuit 20 rises, and when the switch 40 is turned off, the driving power source voltage for the self-excited circuit 20 falls.

The order that is illustrated in FIG. 1 and in which the filter 22 and the comparator 23 are connected may be reversed.

The shorter the rise time ts is, the lower the risk of non-oscillation of the self-excited circuit 20 becomes. Thus, the rise time ts can be shorter. Thus, the FET M1 illustrated in FIG. 2 can have a small gate-source parasitic capacitance and a small gate-drain parasitic capacitance, and thus can operate at high speed.

Figure 4:
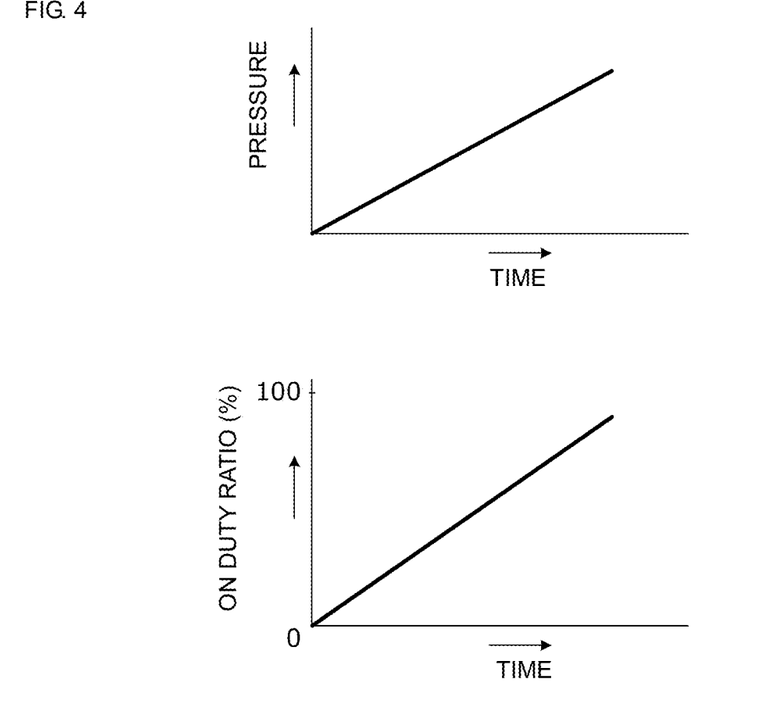
FIG. 4 includes a diagram illustrating changes in an on duty ratio of a driving power source voltage with respect to time elapsed from the startup of the fluid control device 101, and a diagram illustrating changes in a discharge pressure of a piezoelectric pump 10 with respect to the elapsed time.

FIG. 4 includes a diagram illustrating changes in the on duty ratio of the driving power source voltage with respect to time elapsed from the startup of the fluid control device 101, and a diagram illustrating changes in the discharge pressure of the piezoelectric pump 10 with respect to the elapsed time.

As illustrated in FIG. 4, as time elapses from the startup of the fluid control device 101, the on duty ratio of the driving power source voltage (this is also the on duty ratio of the switch 40, and also the on duty ratio of an intermittent operation of the self-excited circuit 20) rises. As a result, the discharge pressure of the piezoelectric pump 10 also rises.

Figure 5:
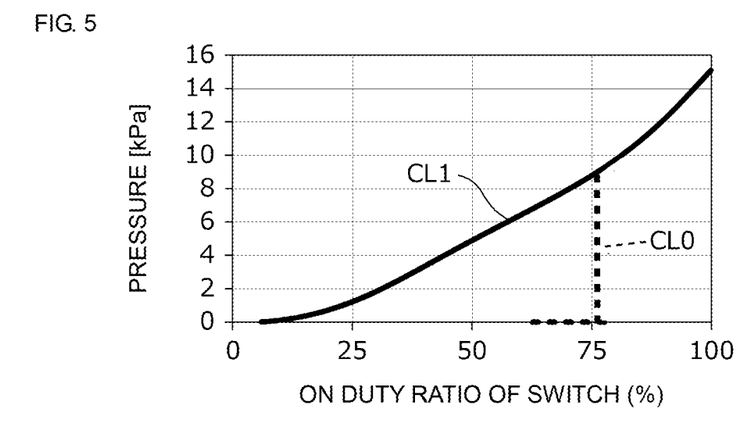
FIG. 5 is a diagram illustrating a relationship between the on duty ratio and the discharge pressure.

FIG. 5 is a diagram illustrating a relationship between the on duty ratio and the discharge pressure. In FIG. 5, a characteristic line CL1 is a diagram representing a relationship between the on duty ratio of the switch 40 and the discharge pressure of the piezoelectric pump. This is an example in which the driving power source voltage is fixed at 8 V, self-excited oscillation occurs from an on duty ratio of 12.5%, that is, a low voltage region as low as an effective voltage of 1 V (8×0.125=1), and the piezoelectric pump operates. As illustrated in FIG. 5, the on duty ratio is roughly proportional to the pressure. Thus, the discharge pressure can be increased from low pressure by controlling the on duty ratio of the driving power source voltage of the self-excited circuit 20. That is, the pressurization speed of the piezoelectric pump can be slowed down.

In contrast to this, in a case where the driving power source voltage is continuously applied (an on duty ratio of 100%) and gradually increased from 0 V under the same conditions, self-excited oscillation starts only when the driving power source voltage is 6 V or higher. When this is converted into an on duty ratio in an 8-V application state, the relationship between the on duty ratio and the discharge pressure is represented by a characteristic line CL0 as in FIG. 5. In this example, the piezoelectric pump operates under the condition that the pressure is greater than or equal to 9.5 kPa. With the method for controlling the driving power source voltage in this manner, an acquired pressure range is narrow and control can be performed only in a high pressure range.

Figure 6:
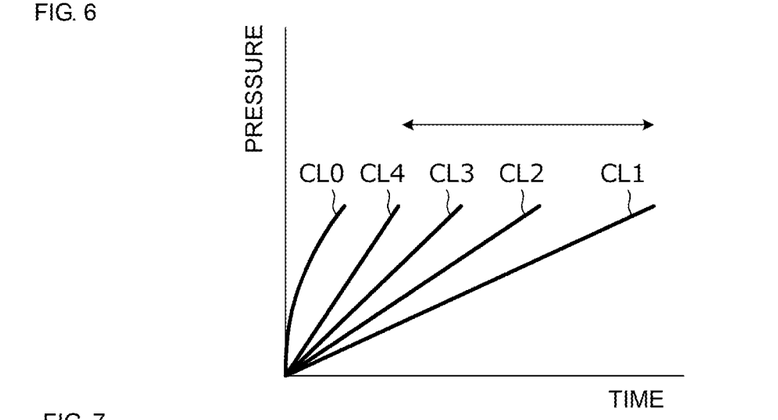
FIG. 6 is a diagram illustrating an example of changes in pressure after the startup of the piezoelectric pump.

FIG. 6 is a diagram illustrating examples of changes in pressure after the startup of the piezoelectric pump. In FIG. 6, all characteristic lines CL1 to CL4 represent examples in which the duty ratio of the driving power source voltage are gradually increased after the startup. The characteristic line CL1 represents an example in which the pressurization speed is set to the slowest speed, and the characteristics line CL4 represents an example in which the pressurization speed is set to the fastest speed. In FIG. 6, the characteristic line CL0 represents an example of a case where the driving power source voltage is continuously applied (an on duty ratio of 100%) and gradually increased from 0 V to 8 V as in the above-described example. With such an existing method, the pressure steeply rises after the startup; however, in the present embodiment, an increase in pressure (pressurization speed) is controlled in accordance with an increase in the duty ratio of the driving power source voltage.

Figure 7:
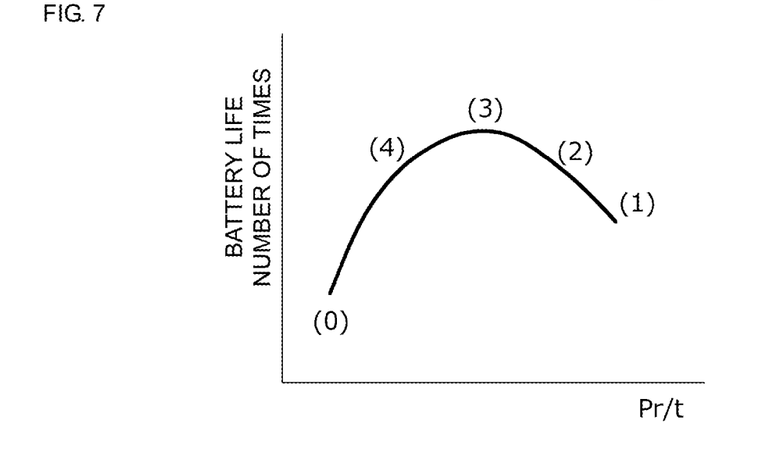
FIG. 7 is a diagram in which the life of an input power source, which is a battery, is represented as the number of times of charge and discharge.

FIG. 7 is a diagram in which the life of the input power source, which is a battery, is represented as the number of times of charge and discharge. The horizontal axis represents the pressurization speed, and the vertical axis represents the battery life of the battery, the battery life meaning that the voltage of the battery is decreased to a termination voltage, which is a predetermined voltage. In FIG. 7, marks (1), (2), (3), (4), and (0) in characteristic curves, each represents the number of times of a corresponding one of the startups corresponding to the characteristic lines CL1, CL2, CL3, CL4, and CL0 illustrated in FIG. 6.

The example of FIG. 7 shows that the battery life becomes longest in a case where pressurization is performed along the characteristic line CL3 of FIG. 6. In this manner, the present embodiment has an advantageous effect in that the battery life is prolonged by performing pressurization at an appropriate pressurization speed.

Figure 8:
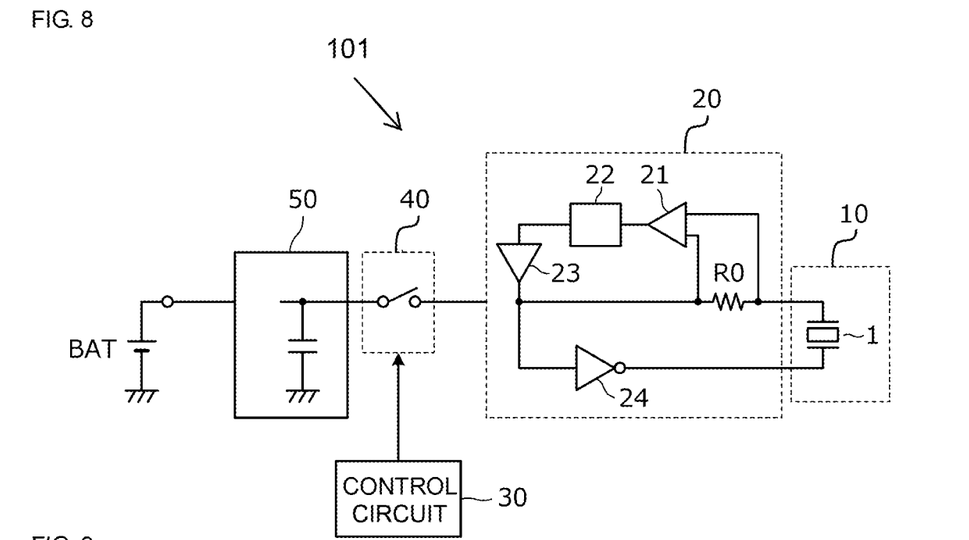
FIG. 8 is a block diagram illustrating the configuration of another fluid control device according to the first embodiment.

FIG. 8 is a block diagram illustrating the configuration of another fluid control device according to the first embodiment. Unlike the example illustrated in FIG. 1, the switch 40 is provided between the DC/DC converter 50 and the self-excited circuit 20. With this configuration, an intermittent voltage of the voltage output from the DC/DC converter 50 is directly applied as the power source voltage of the self-excited circuit 20. Thus, the rise time of the power source voltage of the self-excited circuit 20 is short. Thus, the risk of non-oscillation of the self-excited circuit 20 is greatly decreased. In addition, as a result (because the risk of non-oscillation of the self-excited circuit 20 can be kept low also when ripples or a harmonic component is reduced), the ripples or harmonic component of the output voltage can further be reduced by increasing the capacitance of a capacitor for which shunt connection is provided inside the DC/DC converter 50.

In contrast, the DC/DC converter 50 also operates intermittently with the configuration illustrated in FIG. 1, and thus the configuration illustrated in FIG. 1 consumes less power than that illustrated in FIG. 8.

Figure 9:
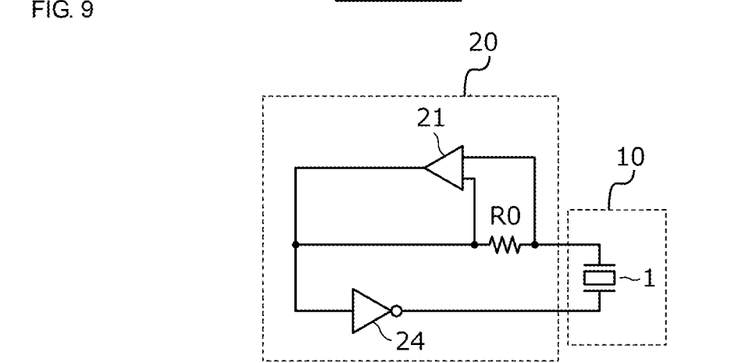
FIG. 9 is a circuit diagram of a self-excited circuit of another fluid control device according to the first embodiment.

FIG. 9 is a circuit diagram of a self-excited circuit of another fluid control device according to the first embodiment. Unlike the example illustrated in FIG. 1, the filter 22 and the comparator 23 are absent. Self-excited oscillation is possible even with such a circuit configuration.

Note that the differential amplifier circuit 21 may have low pass filter characteristics for attenuating a region higher than the oscillation frequency. In addition, either the filter 22 or the comparator 23 illustrated in FIG. 1 may also be added.

Note that, in the examples described above, the examples are described in which the on duty ratio is gradually increased in accordance with time elapsed from the startup of the fluid control device 101, 102. Through this control, the pressurization speed is gradually increased with time elapsed from the startup. Note that the present disclosure is not limited to these examples, and control is possible such that the on duty ratio is gradually decreased in accordance with time elapsed from the startup of the fluid control devices. For example, right after the startup of a fluid control device, assurance of "flow rate" may be more desired than that of "pressure". In such a case, control is possible such that the on duty ratio is set to a little too large value at the time of startup of the fluid control device, the on duty ratio is gradually decreased with time elapsed thereafter, and the pressurization speed of the container is slowed down.

Second Embodiment

In a second embodiment, an example will be described in which not only the duty ratio but also the voltage of the driving power source voltage of the self-excited circuit 20 is changed.

Figure 10:
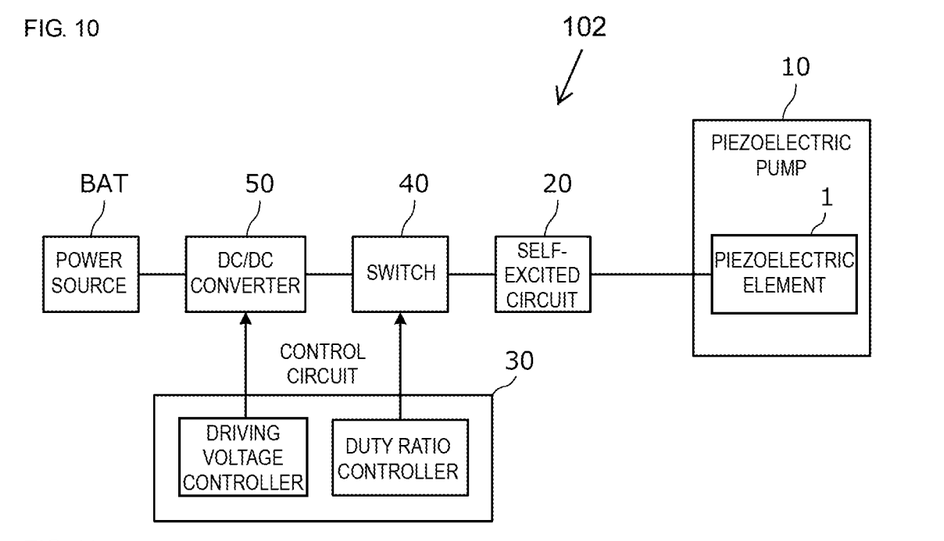
FIG. 10 is a block diagram of a fluid control device 102 according to a second embodiment.

FIG. 10 is a block diagram of a fluid control device 102 according to the second embodiment. The fluid control device 102 includes a piezoelectric pump 10, a self-excited circuit 20, a switch 40, a DC/DC converter 50, and a control circuit 30. The piezoelectric pump 10 includes a piezoelectric element 1. The self-excited circuit 20 performs, upon application of a driving power source voltage thereto, self-excited oscillation to drive the piezoelectric element 1. The switch 40 interrupts the driving power source voltage for the self-excited circuit 20 (switches between application and non-application of the driving power source voltage). The DC/DC converter 50 applies the driving power source voltage to the self-excited circuit 20. The control circuit 30 controls the switch 40 and the DC/DC converter 50.

The DC/DC converter 50 boosts or steps down the voltage of an input power source BAT to apply the driving power source voltage to the self-excited circuit 20. The self-excited circuit 20 performs self-excited oscillation with this driving power source voltage and applies an alternating voltage to the piezoelectric element 1.

In the control circuit 30, a driving voltage controller determines an output voltage through, for example, controlling of the on duty ratio of a switching element of the DC/DC converter 50. In addition, a duty ratio controller determines the on duty ratio of the switch 40.

Figure 11:
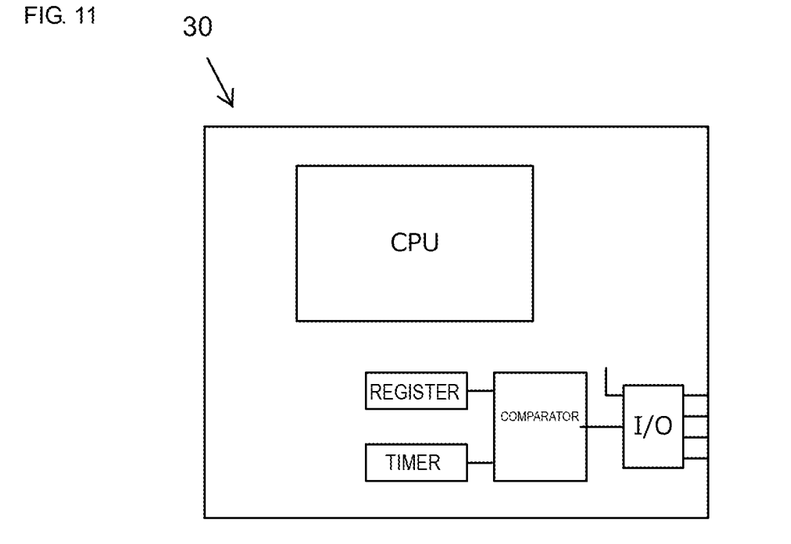
FIG. 11 is a block diagram illustrating the configuration of a main portion of a control circuit 30 in FIG. 10.

FIG. 11 is a block diagram illustrating the configuration of a main portion of the control circuit 30 in FIG. 10. The control circuit 30 includes a micro control unit or microcontroller (MCU), and its I/O ports are connected to the switch 40 and a switching circuit of the DC/DC converter 50. The control circuit 30 includes a register, a timer, and a comparator, and outputs a periodic signal corresponding to a value set in the register, that is, a PWM signal to the switch 40 via the I/O port. Since the counting period of the timer is constant, the switch 40 is turned off and on so as to have a constant period (a constant switching frequency) and at an on duty ratio corresponding to the value set in the register. After the startup, the control circuit 30 increments the value set in the register one by one at a predetermined rate. As a result, the on duty ratio gradually increases.

Figure 12:
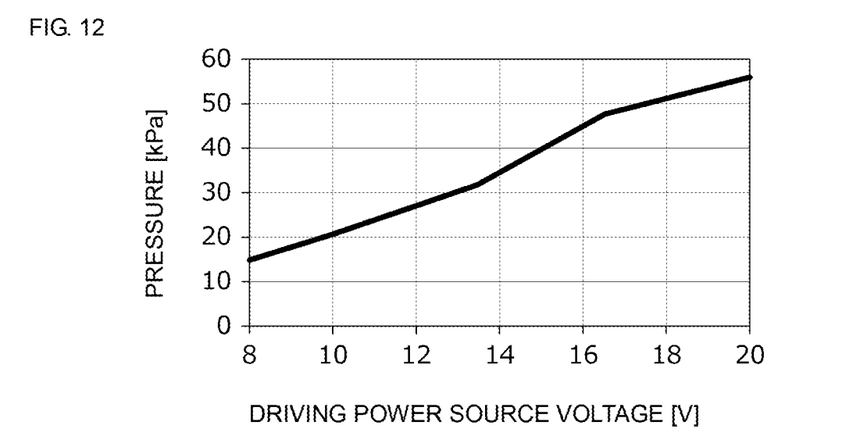
FIG. 12 is a diagram illustrating a relationship between a driving power source voltage of the self-excited circuit 20, that is, an output voltage of a DC/DC converter 50 and a discharge pressure of the piezoelectric pump 10.

FIG. 12 is a diagram illustrating a relationship between the driving power source voltage of the self-excited circuit 20, that is, the output voltage of the DC/DC converter 50 and a discharge pressure of the piezoelectric pump 10. In this example, the on duty ratio is set to 100%. For example, when the driving power source voltage is 8 V, the pressure is 15 kPa, and when the driving power source voltage is 20 V, the pressure is 55 kPa.

In this manner, in a normal range of the driving power source voltage when the piezoelectric pump is used as a pump, the driving power source voltage of the self-excited circuit 20 is roughly proportional to the discharge pressure of the piezoelectric pump 10. After the on duty ratio of the self-excited circuit 20 reaches 100%, the fluid control device 102 of the second embodiment further increases the discharge pressure of the piezoelectric pump by increasing the driving power source voltage.

Figure 13:
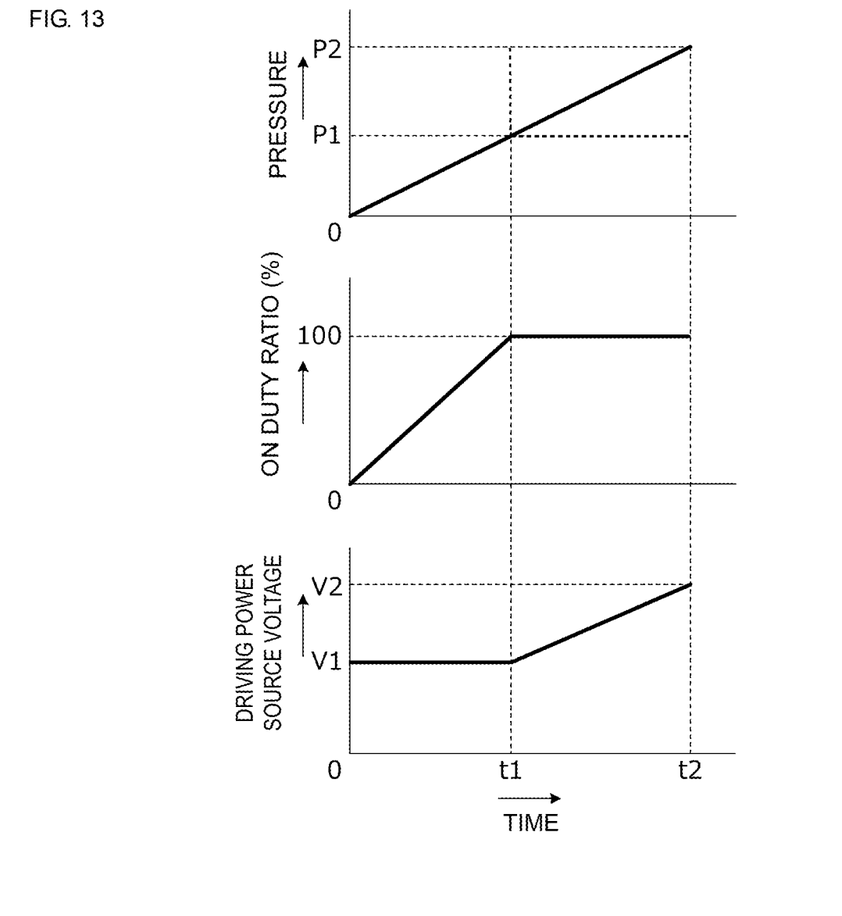
FIG. 13 includes diagrams, each illustrating changes in a corresponding one of pressure, an on duty ratio, and the driving power source voltage with time.

FIG. 13 includes diagrams, each illustrating changes in a corresponding one of the pressure, the on duty ratio, and the driving power source voltage with time. From the startup to t1, the driving power source voltage is set to V1 and the on duty ratio is gradually increased from 0 to 100%. In FIG. 13, a pressure range of 0 to P1 corresponds to "a range in which a necessary pressure is below a predetermined value" in the present disclosure. In addition, a driving power source voltage of V1 corresponds to "the lowest voltage at which the self-excited circuit is operable" in the present disclosure. As a result, the pressure gradually increases from 0 to P1. At and after time t1 (until t2), the on duty ratio is fixed at 100%, the driving power source voltage is gradually increased from V1 to V2. As a result, the pressure gradually increases from P1 to P2. In the end, the pressure slowly increases over a wide range from 0 to P2 after the startup.

According to the present embodiment, since the pressure is continuously controlled over the wide range, pressures can be generated with high accuracy from a predetermined low pressure to intermediate pressures, and to high pressures.

Third Embodiment

In a third embodiment, an example will be described in which the on duty ratio of self-excited oscillation of a self-excited circuit is determined by interrupting a driving voltage for a piezoelectric element.

Figure 14:
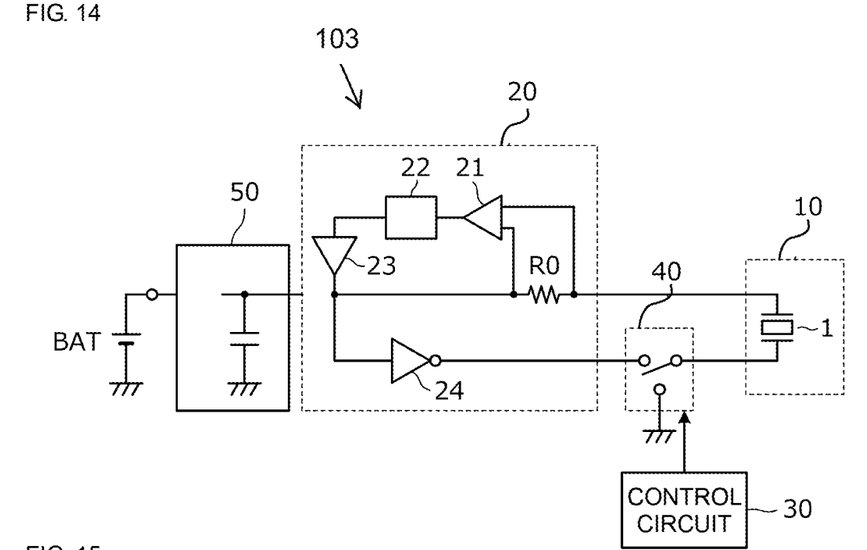
FIG. 14 is a block diagram illustrating the configuration of a fluid control device 103 according to a third embodiment.

FIG. 14 is a block diagram illustrating the configuration of a fluid control device 103 according to the third embodiment. The fluid control device 103 includes a piezoelectric pump 10, a self-excited circuit 20, a DC/DC converter 50, a switch 40, and a control circuit 30. The piezoelectric pump 10 includes a piezoelectric element 1. The self-excited circuit 20 performs, upon application of a driving power source voltage thereto, self-excited oscillation to drive the piezoelectric element 1. The DC/DC converter 50 applies the driving power source voltage to the self-excited circuit 20. The switch 40 interrupts a driving voltage for the piezoelectric element 1. The control circuit 30 switches between states of the switch 40.

Unlike the first embodiment, in the present embodiment, the driving voltage for the piezoelectric element 1 is interrupted while the self-excited circuit 20 keeps performing self-excited oscillation.

An input power source BAT illustrated in FIG. 14 is a battery, and the DC/DC converter 50 boosts this input power source voltage to apply the driving power source voltage to the self-excited circuit 20. The self-excited circuit 20 performs self-excited oscillation with the driving power source voltage. In a state in which the switch 40 is connected to an output of the phase inversion comparator 24 and the piezoelectric element 1 (an on state), the output voltage of the self-excited circuit 20 is applied to the piezoelectric element 1, and in a state in which one end of the piezoelectric element 1 is grounded (an off state), the driving voltage of the piezoelectric element 1 halves. That is, in the first to third embodiments, the piezoelectric element 1 is driven in a balanced manner when the switch 40 is in the on state, and thus double the output voltage of the self-excited circuit 20 is applied to the piezoelectric element 1. In contrast, in the third embodiment, the piezoelectric element 1 is driven in an unbalanced manner when the switch 40 is in the off state, and thus the output voltage of the self-excited circuit 20 is applied on an as is basis to the piezoelectric element 1.

The configuration of the DC/DC converter 50 and that of the self-excited circuit 20 are the same as those illustrated in the first embodiment.

According to the present embodiment, on/off of the driving voltage for the piezoelectric element 1 can be switched at higher speed than with the configuration for interrupting the driving voltage for the self-excited circuit 20 (FIG. 1), and thus fluid control is performed by the piezoelectric pump 10 with high accuracy. Thus, in a case where the fluid control device 103 is applied to, for example, a sphygmomanometer, the accuracy of blood pressure measurement can be increased.

Fourth Embodiment

Figure 15:
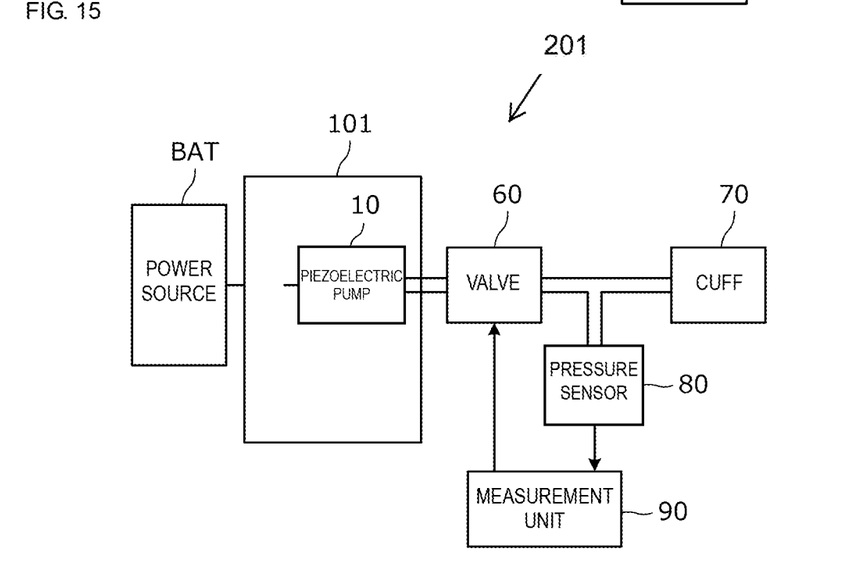
FIG. 15 is a block diagram of a sphygmomanometer 201 according to a fourth embodiment.

In a fourth embodiment, a sphygmomanometer will be described. FIG. 15 is a block diagram of a sphygmomanometer 201 according to the fourth embodiment. The sphygmomanometer 201 includes a fluid control device 101, a power source BAT therefor, a valve 60, a cuff 70, a pressure sensor 80, and a measurement unit 90.

The configuration of the fluid control device 101 is the same as that illustrated in the first embodiment. The cuff 70 is connected to a discharge unit of the piezoelectric pump 10 of the fluid control device 101 with the valve 60 interposed therebetween. The pressure sensor 80 detects an air pressure of the cuff 70. In a state in which the piezoelectric pump 10 discharges air, the valve 60 sends the air to the cuff, and in a case where the air pressure of the cuff is reduced, the valve 60 releases the air into the atmosphere at a predetermined flow rate. The measurement unit 90 (e.g., a controller) detects pulse waves on the basis of a detection value from the pressure sensor in a pressurization process and determines the maximum blood pressure and the minimum blood pressure on the basis of the oscillometric method. Thereafter, the air is removed from the valve 60 in a pressure release process. In this manner, a method for measuring a blood pressure in a pressurization process can exhaust air rapidly in a pressure release process after the measurement, and thus total time required for blood pressure measurement is short, and current consumption is low since the battery is consumed only during boosting time. Note that, pressurization to a predetermined pressure may be performed in the pressurization process for the cuff, and a blood pressure may be measured in a subsequent pressure release process.

Lastly, the embodiments described above are examples in every respect and are not limited thereto. Those skilled in the art may deform and make changes as needed. The scope of the present disclosure is represented not by the embodiments described above but by claims. Furthermore, the scope of the present disclosure includes changes from embodiments within the scope of the claims and the scope of equivalents of the claims.

REFERENCE SIGNS LIST

BAT input power source
R0 output current detection resistor
R1, R2, R3, R4 resistor
1 piezoelectric element
10 piezoelectric pump
20 self-excited circuit
21 differential amplifier circuit
22 filter
23 comparator
24 phase inversion comparator
30 control circuit
40 switch
50 DC/DC converter
60 valve
70 cuff
80 pressure sensor
90 measurement unit
101, 102, 103 fluid control device
201 sphygmomanometer

The invention claimed is:

1. A fluid control device comprising:
   a piezoelectric pump comprising a piezoelectric element;
   a self-excited circuit configured to, upon application of a driving power source voltage, self-excitedly oscillate and apply a driving voltage to the piezoelectric element, thereby driving the piezoelectric element; and
   a control circuit configured to determine an on-time duty ratio for driving the piezoelectric element,
   wherein when a desired operating pressure of the piezoelectric pump is below a predetermined value, the on-time duty ratio corresponds to a ratio at which the applied driving power source voltage is a lowest voltage at which the self-excited circuit is operable, and
   when the desired operating pressure of the piezoelectric pump is greater than or equal to the predetermined value, the driving power source voltage is greater than a lowest voltage corresponding to an on-time duty ratio of 100%.

2. The fluid control device according to claim 1, further comprising:
   a switch configured to selectively apply or interrupt the application of the driving power source voltage to the self-excited circuit.

3. The fluid control device according to claim 2, wherein the control circuit is further configured to change a state of the switch according to the on-time duty ratio.

4. A sphygmomanometer comprising:
a cuff;
the fluid control device of claim 3 configured to pressurize the cuff by an output of the piezoelectric pump;
a valve configured to adjust pressure inside the cuff by controlling a supply of the output of the piezoelectric pump; and
a controller and a sensor together configured to measure a blood pressure of a subject based on the pressure of the cuff,
wherein the control circuit is further configured to change a state of the switch at a predetermined frequency.

5. The sphygmomanometer according to claim 4, wherein the frequency is greater than or equal to ten times a reciprocal of a measurement period of the controller and sensor, and is less than or equal to one tenth a driving frequency of the piezoelectric element.

6. The fluid control device according to claim 2, wherein the switch comprises:
a field-effect transistor (FET), and
a circuit configured to drive the FET according to the on-time duty ratio.

7. The fluid control device according to claim 1, further comprising:
a switch configured to selectively apply or interrupt the application of the driving voltage to the piezoelectric element.

8. The fluid control device according to claim 7, wherein the control circuit is further configured to change a state of the switch according to the on-time duty ratio.

9. The fluid control device according to claim 7, wherein the switch comprises:
a field-effect transistor (FET), and
a circuit configured to drive the FET according to the on-time duty ratio.

10. The fluid control device according to claim 1, wherein the on-time duty ratio is predetermined.

11. The fluid control device according to claim 1, further comprising:
a DC/DC converter configured to convert a DC input power source voltage to the driving power source voltage.

12. The fluid control device according to claim 11, wherein the control circuit is further configured to selectively control output of the driving power source voltage from the DC/DC converter according to the on-time duty ratio.

13. The fluid control device according to claim 1, wherein the control circuit comprises a microcontroller including a pulse width modulation (PWM) signal generation circuit configured to generate a PWM signal, wherein the on-time duty ratio corresponds to the PWM signal.

14. A sphygmomanometer comprising:
a cuff;
the fluid control device of claim 1 configured to pressurize the cuff by an output of the piezoelectric pump;
a valve configured to adjust pressure inside the cuff by controlling a supply of the output of the piezoelectric pump; and
a controller and a sensor together configured to measure a blood pressure of a subject based on the pressure of the cuff.

15. The sphygmomanometer according to claim 14, wherein the sensor is configured to measure the blood pressure of the subject based further on a pulse wave of the subject or Korotkoff sounds.

* * * * *